(12) United States Patent
Heaton et al.

(10) Patent No.: US 6,942,687 B1
(45) Date of Patent: Sep. 13, 2005

(54) PATIENT COOLING ENCLOSURE

(75) Inventors: Keith Patrick Heaton, Poole (GB); Kenneth William Hunt, Wimborne (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 10/398,338

(22) PCT Filed: Nov. 5, 1999

(86) PCT No.: PCT/GB99/03688

§ 371 (c)(1), (2), (4) Date: Mar. 25, 2003

(87) PCT Pub. No.: WO00/27323

PCT Pub. Date: May 18, 2000

(51) Int. Cl.[7] .................................. A61F 7/00
(52) U.S. Cl. ...................... 607/107; 607/108
(58) Field of Search ............... 607/96, 104, 107–112; 407/108–112

(56) References Cited

U.S. PATENT DOCUMENTS

| | | |
|---|---|---|
| 3,085,405 A | 4/1963 | Frantti |
| 3,283,520 A | 11/1966 | Donohue et al. |
| 3,610,323 A | 10/1971 | Troyer |
| 3,738,367 A | 6/1973 | Hardy |
| 3,999,541 A | 12/1976 | Tabor |
| 4,170,998 A | 10/1979 | Sauder |
| 4,353,359 A | 10/1982 | Milbauer |
| 4,423,308 A | 12/1983 | Callaway et al. |
| 4,506,511 A | 3/1985 | Cameto et al. |
| 4,525,885 A | 7/1985 | Hunt et al. |
| 4,572,188 A | 2/1986 | Augustine et al. |
| 4,638,519 A | 1/1987 | Hess |
| 4,660,388 A | 4/1987 | Greene |
| 4,777,802 A | 10/1988 | Feher |
| 4,867,230 A | 9/1989 | Voss |
| 4,907,308 A | 3/1990 | Leininger et al. |
| 4,966,145 A | 10/1990 | Kikumoto et al. |
| 4,987,896 A | 1/1991 | Nakamatsu |
| 5,035,241 A | 7/1991 | Walasek et al. |
| 5,044,364 A | 9/1991 | Crowther |
| 5,081,339 A | 1/1992 | Stine |
| 5,097,548 A | 3/1992 | Heck et al. |
| 5,125,238 A | 6/1992 | Ragan et al. |
| 5,165,127 A | 11/1992 | Nicholson |
| 5,300,098 A | 4/1994 | Philipot |
| 5,350,417 A | 9/1994 | Augustine |
| 5,383,918 A * | 1/1995 | Panetta .................. 607/104 |
| 5,392,847 A | 2/1995 | Stephenson |
| 5,396,671 A | 3/1995 | Stacy |
| 5,405,370 A * | 4/1995 | Irani ..................... 607/104 |
| 5,438,707 A * | 8/1995 | Horn ........................ 2/457 |
| 5,473,783 A | 12/1995 | Allen |
| 5,655,237 A | 8/1997 | Suzuki et al. |
| 5,674,269 A * | 10/1997 | Augustine ............... 607/107 |
| 5,699,570 A | 12/1997 | Wilkinson et al. |

(Continued)

FOREIGN PATENT DOCUMENTS

CA  2 254 999  4/2002

(Continued)

Primary Examiner—Roy D. Gibson

(57) ABSTRACT

An enclosure is described for containing a patient whose core temperature is to be cooled below normal body temperature, e.g. to reduce brain damage in patients suffering cardiac arrest. The enclosure comprises a base panel and one or more side panels attached to the base panel, the side panels being foldable over the patient to create an enclosure. Air conduits are provided on one or more panels with outlets positioned to direct cold air onto areas of the patient from which heat loss is particularly rapid.

15 Claims, 7 Drawing Sheets

U.S. PATENT DOCUMENTS

| | | |
|---|---|---|
| 5,749,109 A | 5/1998 | Kappel et al. |
| 5,817,147 A | 10/1998 | Wolf |
| 5,891,187 A * | 4/1999 | Winthrop et al. .............. 607/96 |
| 6,001,057 A | 12/1999 | Bongiovanni et al. |
| 6,210,427 B1 | 4/2001 | Augustine et al. |
| 6,277,144 B1 * | 8/2001 | Tomic-Edgar et al. ...... 607/108 |
| 6,282,737 B1 | 9/2001 | Vrzalik |
| 6,375,673 B1 * | 4/2002 | Clifton et al. .............. 607/104 |
| 6,730,115 B1 | 5/2004 | Heaton |
| 2004/0093050 A1 | 5/2004 | Beard et al. |

FOREIGN PATENT DOCUMENTS

| | | |
|---|---|---|
| EP | 0 898 473 | 3/2004 |
| FR | 2 754 167 | 4/1998 |
| GB | 783350 | 9/1957 |
| GB | 2 263 872 | 8/1993 |
| GB | 2 284 555 | 6/1995 |
| GB | 2 313 549 | 12/1997 |
| GB | 2 343 377 | 7/2003 |
| WO | WO 95/10211 | 4/1995 |
| WO | WO 97/14380 | 4/1997 |
| WO | WO 97/24088 | 7/1997 |
| WO | WO 97/42919 | 11/1997 |
| WO | WO 00/27323 | 5/2000 |

* cited by examiner

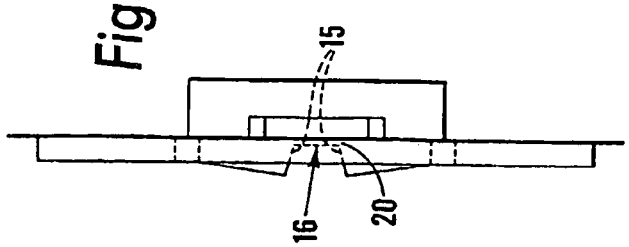
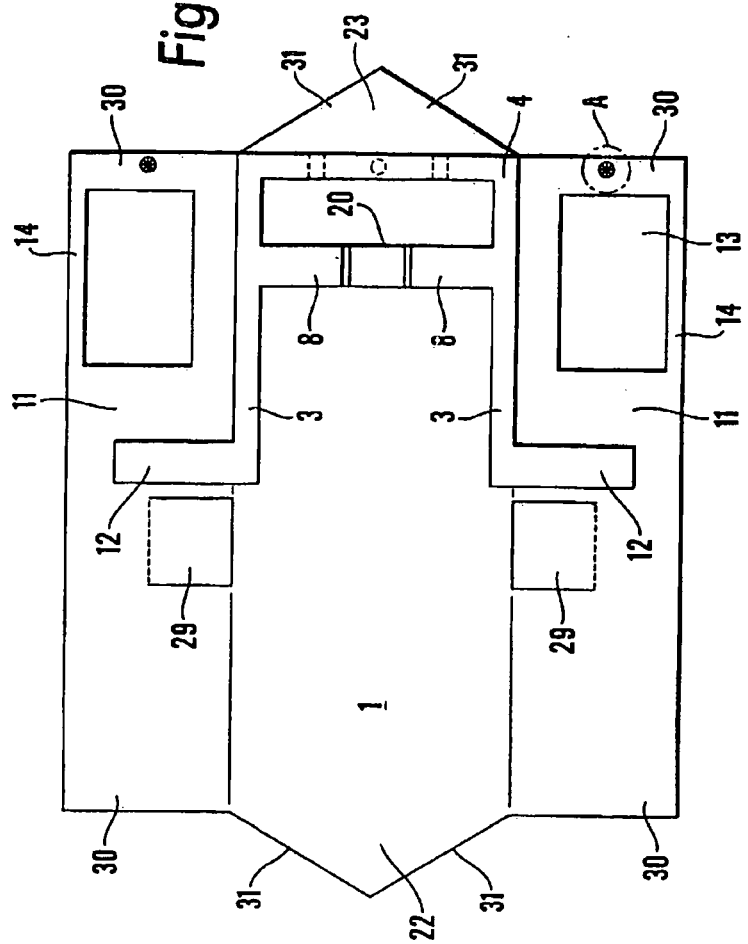

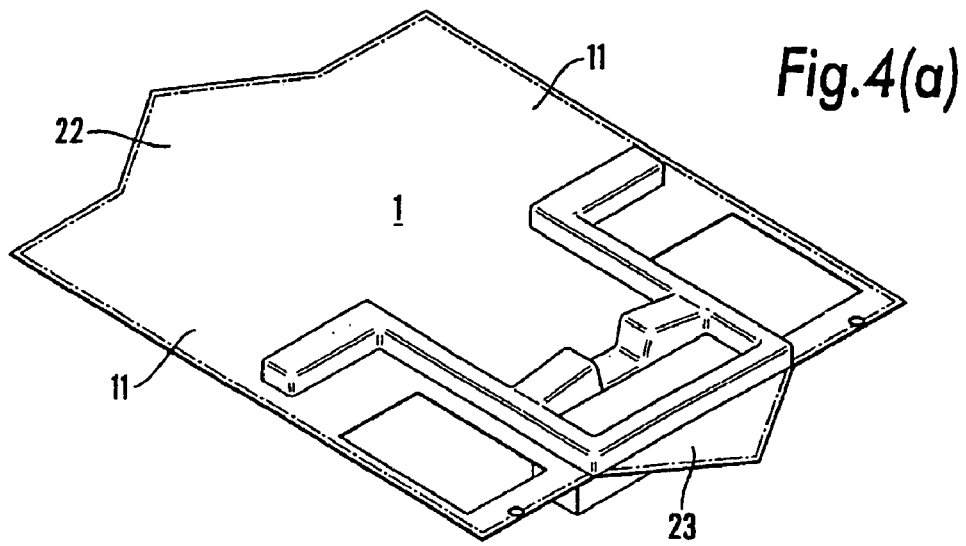
*Fig.4(a)*
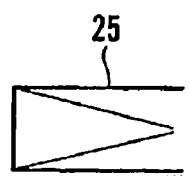
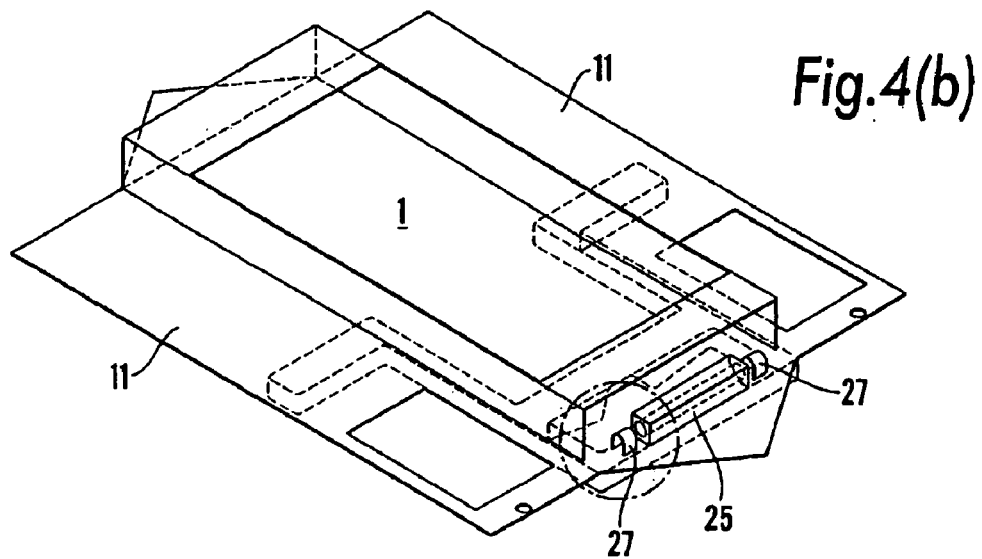
*Fig.4(b)*

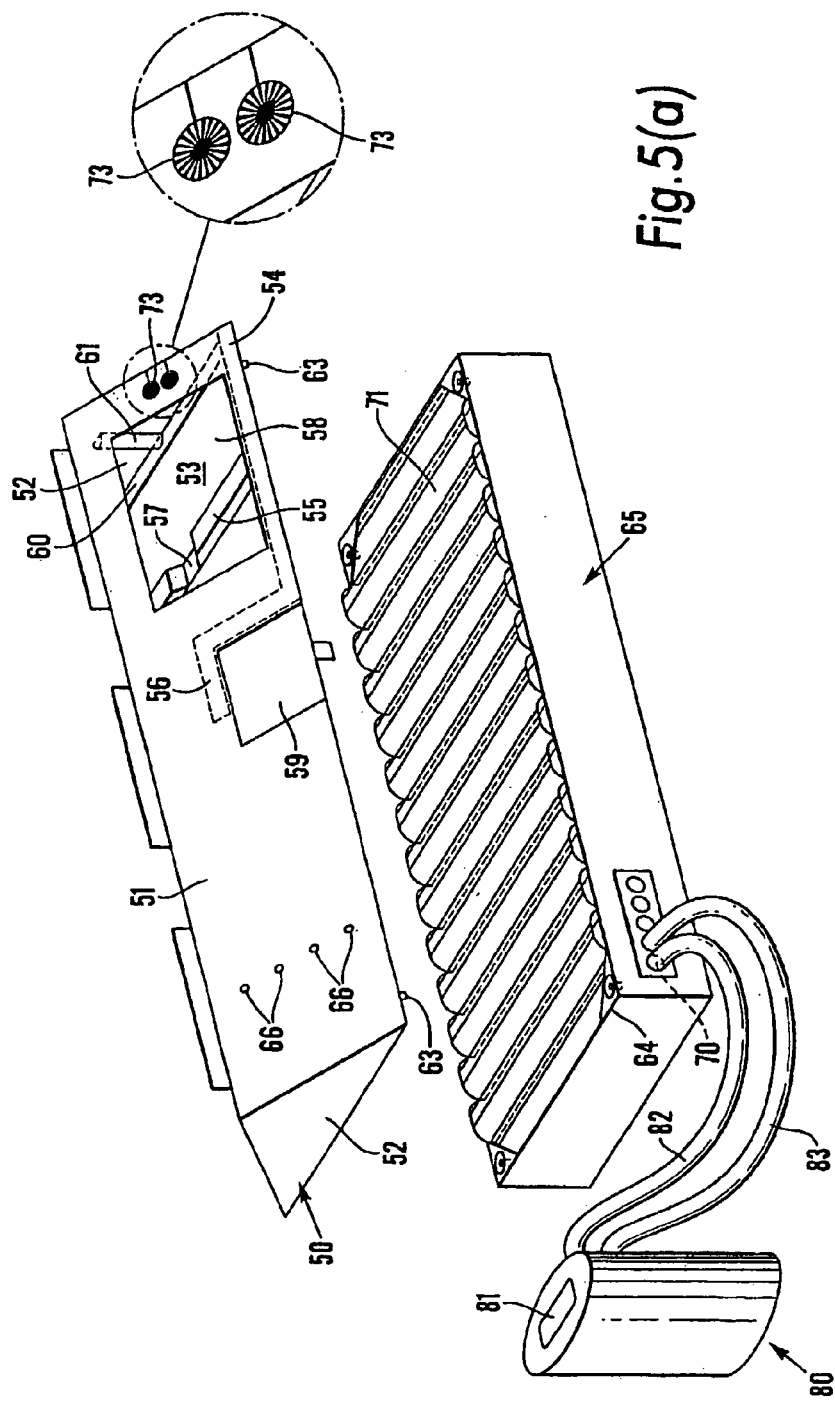

PATIENT COOLING ENCLOSURE

This invention relates to an enclosure or tent for containing a patient to be cooled to a core temperature below normal body temperature.

In our co-pending patent application WO 97/42919 there is described a system for cooling the patient to a core temperature which is a few degrees below normal blood temperature, e.g. in the range of about 32 to 34° C. This clinical procedure has been used with some success in reducing brain damage to cardiac or stroke patients as a result of reduced flow of oxygenated blood.

It is an object of the present invention to provide an improved enclosure or tent which is effective in rapidly reducing the core temperature to the desired range. In such treatment procedures, it is crucial to start the cooling procedure as rapidly as possible and, also, to bring the patient's body temperature down very quickly. The present invention seeks to provide an enclosure which, in at least one embodiment, can be used for such cooling purposes on a variety of supports, including within an ambulance fitted with a source of cold air.

According to the present invention there is provided apparatus for cooling a patient to a core temperature below normal body temperature which comprises a first, flexible panel for receiving the patient, one or more other flexible panels which are connected to the first panel and which are foldable over the patient to form an enclosure, at least one conduit connected to a source of refrigerated air, said first panel being supported on a mattress comprising a plurality of air inflated sacs, said conduit being connected to one or more outlets for directing a stream of air onto the patient's body.

Conveniently, the first flexible panel is in the form of a base panel for receiving the patient and the one or more other flexible panels comprise one or more upper panels which are joined to the base panel to create an enclosure. The upper panels may be permanently connected along one edge, e.g. by sewing or welding to the base panel and the enclosure formed by joining the upper panels together by means of a suitable releasable fastening to form a tent-like enclosure. Other alternatives are possible. For example, a single upper panel may be joined by permanent fastening along one edge to the base panel, and by a releasable fastening along its opposite edge to the base panel. As a further modification, the upper panel may be attached at both edges to opposite edges of the base panel by releasable fastenings.

Preferably, a first panel incorporates one or more header tubes extending longitudinally with respect to the panel. This tube or tubes is connected to outlets for cold air so that these outlets may be fed with cold air connected to the header tubes from at least one end of the enclosure. The parts of the patient's body from which body heat is removed most rapidly and effectively are those areas where blood vessels are closest to the skin, for example, the neck and groin areas. Therefore, the outlets are preferably directed especially to these areas.

Conveniently, the base panel incorporates one or more flaps, webs or cords for attachment of the tent or enclosure to a mattress or bed.

According to another aspect of the invention there is provided an enclosure for use in cooling a patient to a core temperature below normal body temperature, said enclosure comprising side and end panels and airways for directing cold air on parts of the patient's body from which heat loss is rapid, and header conduits for feeding cold air to the airways.

It is important for maximum effectiveness and uniformity of cooling that the material forming the walls of the enclosure do not directly contact the patient (except the surface on which the patient's body rests), but provides a convective space around the patient.

According to the various aspects of the invention the enclosure has a shape and size such that it covers the major part of the patient's body. Preferably, the enclosure is arranged to cover at least the patient's torso, including the groin and upper legs, as well as the neck. The patient's face may be left exposed to facilitate access to the mouth and nose, e.g. for ventilating the patient's lungs. In this case, the enclosure may be sealed against air loss around the patient's neck.

Conveniently, the enclosure includes quick-release or snap connectors for connecting the header conduits to the refrigerated air supply for the mattress or for a separate refrigerated air supply.

The mattress is preferably a low air loss mattress and the enclosure is provided with male connectors which are adapted to engage with female connectors located adjacent the mattress. The connectors on the mattress may be specifically provided for engaging with the enclosure to supply refrigerated air thereto. Alternatively, the feed connectors on the enclosure may be engageable with the connectors for supplying air to the sacs of a low air loss mattress, so that by, for example, removing the sacs at the extreme ends of the mattress, the feed connectors of the enclosure can be connected in their place to provide a feed of cold air to the interior of the enclosure.

Embodiments of enclosures in accordance with the invention will now be described by way of example only, with reference to the accompanying drawings, in which:

FIG. 1 shows a patient lying on the base panel of an enclosure,

FIGS. 2(a), 2(b) and 2(c) show plan, end and side views of a modified form of the unassembled enclosure shown in FIG. 1, FIG. 3 is a perspective view of the assembled enclosure shown in FIGS. 2(a) to 2(c), FIGS. 4(a) and 4(b) are respectively plan and underside views of the unassembled enclosure;

FIG. 5(a) is an exploded perspective view, partly in section, showing another embodiment of the enclosure arranged for fitting to a low air loss mattress.

Figure 1:
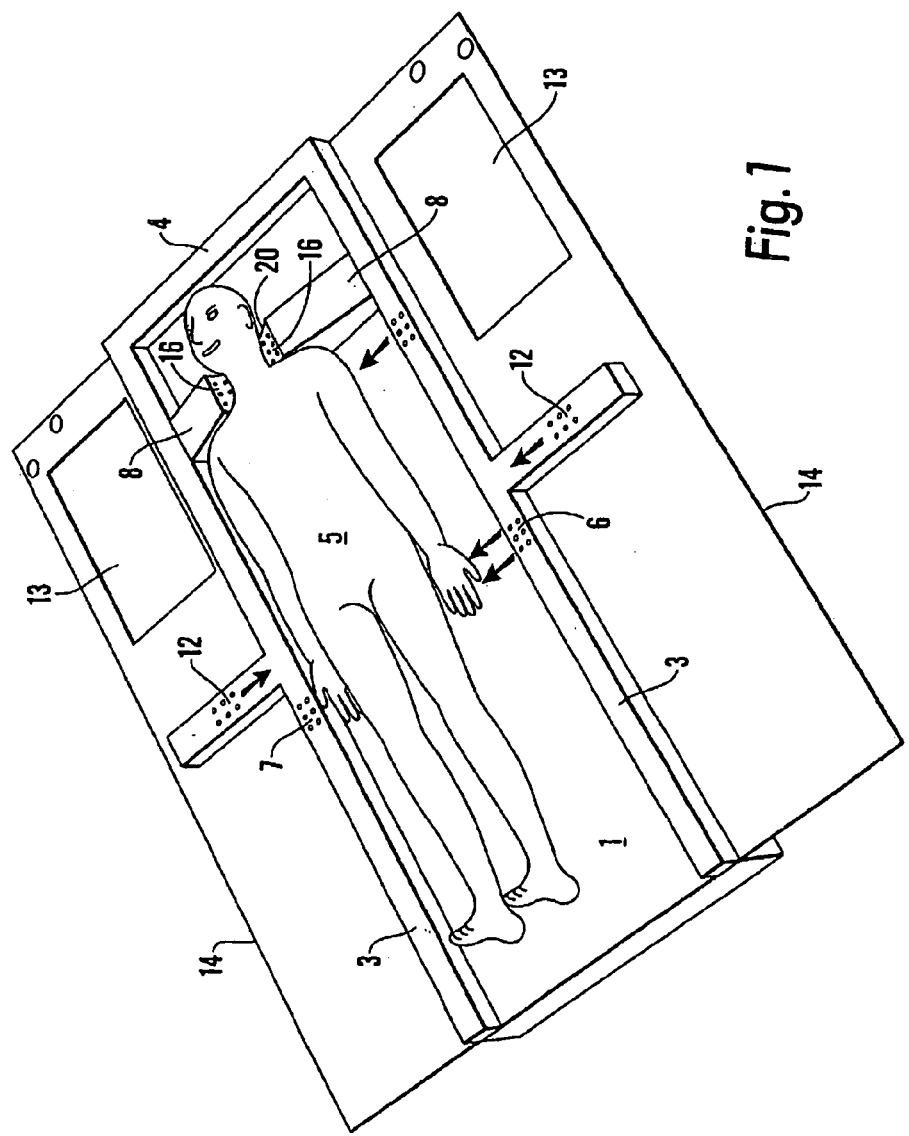

Referring to the drawings, the enclosure is shown in its opened out form in FIGS. 1, 2(a) to 2(c), 4(a) and 4(b) and comprises a first panel (1) intended to be supported on a separate mattress base. Extending longitudinally of the panel (1) are a pair of header tubes (3) for feeding cold air to a patient (5) supported on the panel (1) of the mattress (2). The header tubes (3) are connected by a cross tube or plenum chamber (4) which is fed with cold air from a heat exchanger as described in our prior application WO 97/42919. Header tubes (3) are provided with outlets for cold air such as indicted as locations (6) and (7). The ends of header tubes (3) which are remote from the plenum chamber (4) may be connected to exhaust valves which can be pre-set or may be manually adjustable or automatically controlled to provide for a desired through put of cold air through the header tubes (3). In order to locate the position of the patient's head in relation to cold air outlets, the panel may incorporate blocks (8) extending laterally of the patient. These blocks may be inflatable and be connected to the headers and incorporate perforations (15) (see FIG. 2(b)) at the ends adjacent to the patient's neck, so that cold air is blown directly onto the patient's neck area. As shown more clearly in FIGS. 2(a) and 2(b), the blocks (8) may be joined by an airway (20) which extends beneath the patient's neck. Airway (20) may also include perforations (16). Thus, the patient's neck area will be subjected to streams of cold air projected at the patient's neck at the sides and, if desired, also around the back.

Figure 3:
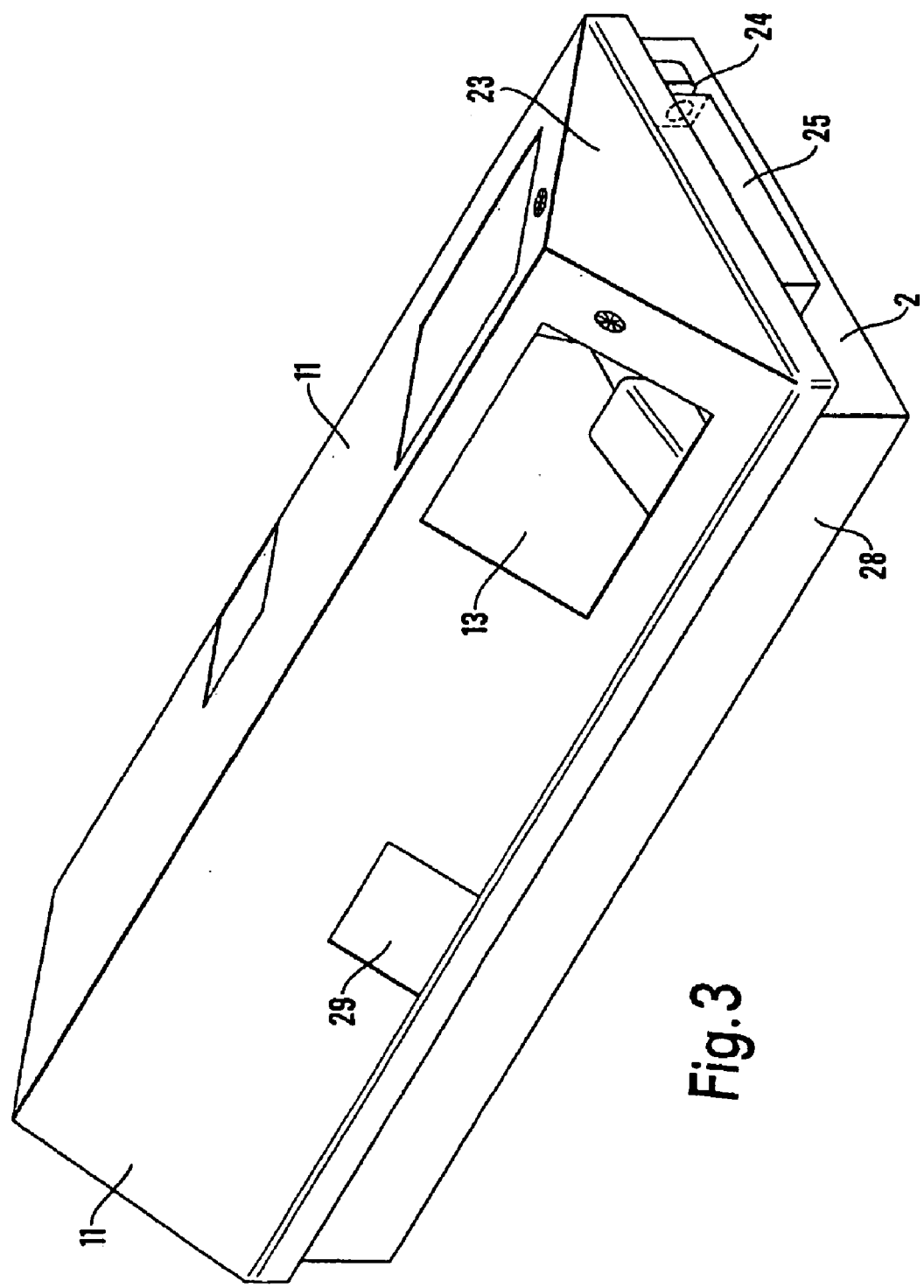

Flexibly attached to the panel (1) or to the headers (3) are lateral panels (11). Panels (11) include tubular extensions (12) connected to the headers (3). The extensions (12) may also incorporate perforations so that when panels (11) are folded over the patient, cold air is emitted from the extensions (12) and blow over the upper leg and lower torso area of the patient. Alternatively, perforations may be formed in the headers (3) at locations (6) and (7), as shown in FIG. 1. The lower panel may incorporate a cross tube passing beneath the patient's upper legs and crotch area which is connected to one or both headers (3), and has perforations for directing cold air onto these areas of the patient's body. The inflated tubular extensions (12), when folded towards each other, lift the panels off the patient's body and help to support the side panels in a tent-like structure, which is best seen in FIG. 3. Panels (11) incorporate windows (13), e.g. of transparent plastic, for observing the patient when the enclosure is closed. Quick fastening means such as strips of miniature hooks and eyes, e.g. Velcro® strips, may be attached to the lateral edges (14) of the panels (11), so that when they are folded over the patient, a closed enclosure can be rapidly formed. Alternative re-sealable fastening means include pressure-sensitive adhesive strips, magnetic tapes and flexible beads and grooves. Windows (13) may be openable (and, e.g. re-sealable with Velcro® strips) to permit easy access to the patient's nose and mouth.

FIGS. 2(a) to 2(c) and 3 and 4(a), 4(b) differ from the enclosure shown in FIG. 1 essentially in that the headers (3) do not extend the whole length of the panel (1). The same reference numerals are used as in FIG. 1 to indicate equivalent parts. As can be seen in FIGS. 2(a), 4(a) and 4(b), the lower panel (1) has triangular flaps (22 & 23) attached at each end. These flaps are folded up and joined to the panels (11) to form the assembled enclosure as seen in FIG. 3. Velcro® strips on adjoining edges (30) of panels (11) and edges (31) of flaps (22) and (23), enable a quick release tent-like enclosure to be created. It has been found in practice that cooling the legs makes little difference to the cooling rate of the patient and that the most effective areas to concentrate on are the neck and shoulder area, the thighs (particularly the inner thighs) and the lower abdomen. Outlets for refrigerated air are therefore preferably provided to impinge on these areas.

The enclosure may be connected at one or both ends to a source of cold air such as the refrigeration and blower unit described in our above PCT application. In FIG. 3, a connection point for a cold air conduit is indicated at (24). The connection point (24) leads into a manifold chamber (25) which communicates with the cross member (4).

Figure 4C:
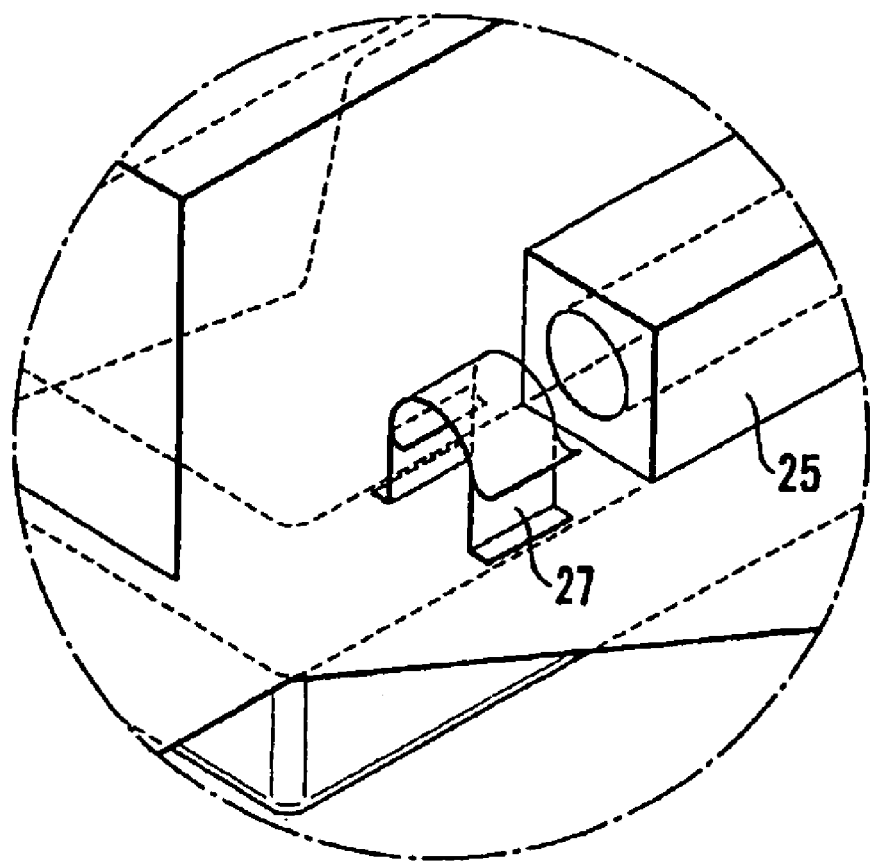
FIG. 4(c) is a detail view of the enclosure of FIGS. 4(a) and 4(b) showing one method of attaching a supply conduit.

In FIGS. 4(b) and 4(c), the arrangement is slightly different in that provision is made for connecting a supply conduit at either end of the chamber (25), a 'duck bill' valve is fitted to each end of the chamber (25) which automatically closes when air is present inside the chamber. The valve is opened by inserting a supply conduit into the valve. A support loop (27) provides a quick attachment system for attaching a supply conduit to the manifold chamber.

The enclosure is mounted on a low air support mattress which is also fed with a continuous flow of cold air. In other words, the sacs of the mattress are pressurised with refrigerated air and the cold air flows continuously through the sacs in order to maintain a lowered temperature in the patient supporting sacs. The enclosure may be temporarily secured by loops or flaps (28) to the underlying mattress or bed. The side panels may also include openable panels (29) for access to the lower part of the patient.

The assembly of the panel (1), tubular headers (3) and panels (11) is conveniently formed from a disposable material such as a non-woven plastics material, e.g. polypropylene, or paper which may be reinforced or coated for additional strength. Manufacture of the enclosure as a substantially flat sheet of interconnected panels and inflatable ribs and tubes is advantageous for transport and storage, and can be readily assembled on a suitable support, such as a mattress. However, the enclosure may be manufactured in a pre-assembled state and, in this case, Velcro® strips or other closure means are then unnecessary to join the side panels to form an enclosed space. In such a case, the joins between the panels may be formed by gluing, stitching or welding.

FIGS. 5(a) to 5(d) show a further embodiment of an enclosure in accordance with the invention.

Figure 5B:
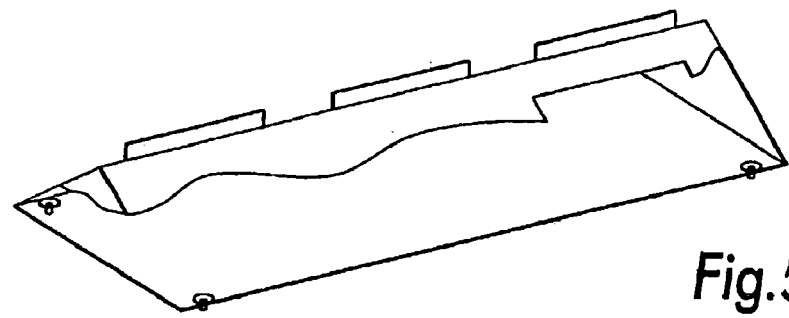
FIGS. 5(b) to 5(d) are perspective views of the enclosure showing different aspects of the enclosure.
Figure 5C:
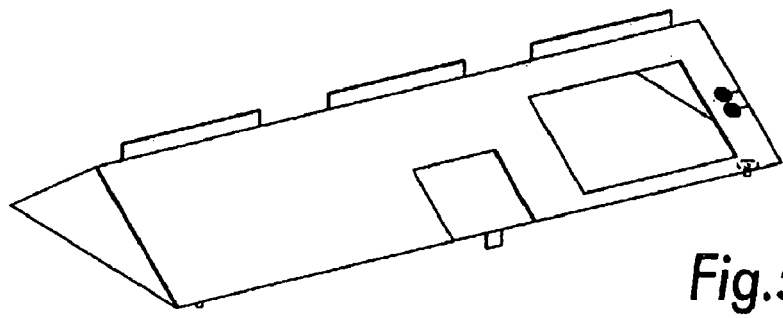
Figure 5D:
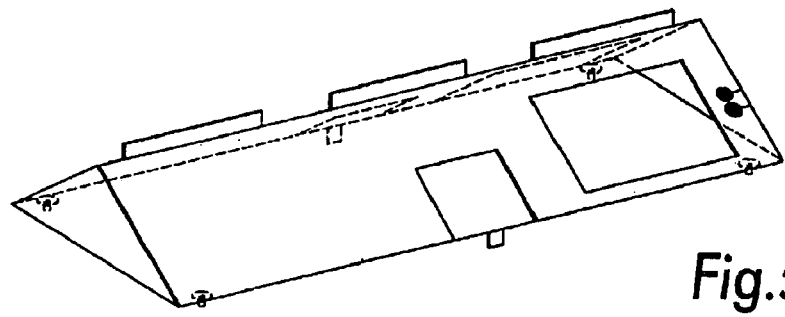

Referring to FIGS. 5(a) to 5(d), the enclosure (50) is generally tubular or wedge-shaped of a suitable length and height to accommodate a supine person. Enclosure (50) is formed from sloping lateral panels (51) and sloping or upright end panels (52). Panels (51) and (52) are preferably double-skinned as indicated in FIG. 5(b), to provide for enhanced insulation. A base panel (53) is also provided and the entire enclosure is fabricated as a disposable item intended for use by a single patient. Longitudinal header conduits (54) are arranged to supply air to a transverse conduit (55) which is shaped at (57) to partially encompass the neck area of a patient. Portion (57) is apertured to direct a stream of refrigerated air onto the patient's neck. Headers (54) also communicate with a conduit (56) which is adapted to direct refrigerated air onto a patient's groin and lower abdomen area through appropriately placed apertures. One or more access windows (58) e.g. of clear plastic are provided for monitoring the patient's condition. Access panels (59) may also be provided for facilitating access to the patient and, for example, for connecting catheters and monitoring equipment to the patient. Access holes (73) are provided for ventilator hoses to supply ventilation air or oxygen to the patient or for catheters or sensors to monitor, the patient's vital functions. The access holes (73) are segmented as shown in the enlarged view to provide an automatic seal around the hose. The slit allows the hoses or other lines to be secured without disconnection. The header conduits may include a bridging portion (60) and in the illustrated embodiment, the bridging portion feeds air to an inflatable rib (61) to assist in supporting the end panel (52) when the access covers (58) and/or (59) are open.

Refrigerated air is supplied to the enclosure through connectors (63) located at the lower corners. Each connector (63) is a male connector half which is adapted to engage in a corresponding female connector half (64) positioned at the corners of an inflatable mattress (65). Suitable connectors are of the kind described in GB published application No. 2070174. Connector halves (64) are supplied with refrigerated air from a refrigerator and a blower unit (80). The refrigerator and blower unit may be of the kind described in WO 97/42919, and include control means and a control panel (81) for controlling and displaying the temperature of the refrigerated air emitted from the unit. The control means may also control other parameters such as flow rates of refrigerated air and pressures within the, air sacs (71) forming the mattress. Temperature detectors within the enclosure may be linked to the unit (80) so that the temperature and rate of flow of refrigerated air can be programmed to achieve a desired or target temperature within the enclosure. Typically, the temperature of the refrigerated air may be selected to achieve a target temperature of 8–12° C. in the enclosure. It has been found that this can be achieved rapidly with the enclosures of the invention by feeding the enclosure with air at about 5 to 8° C. and at a feed rate of 10~20 cubic feet per minute (0.283~0.566 cubic meters per minute). Approximately 1 kilowatt of cooling power is employed. The supply of refrigerated air is conducted to the mattress via flexible tubes (82), (83), air inlet sockets (70) and conduits internal of the mattress to the connector halves (64). In order to regulate the flow of refrigerated air to the enclosure, some of the connectors (64) are arranged to feed air to the enclosure, while others are arranged to exhaust air from the enclosure. For example, the connectors (64) at the head of the mattress may feed cold air to cross tube (60), while the connectors at the foot exhaust air from the enclosure. Alternatively, the connectors (64) at one side may provide the feed, while those on the other side exhaust air from the enclosure. Appropriately arranged feed and exhaust valves may be manually or automatically controlled to ensure that the patient is subjected to the correct level of cooling effect to reduce his core temperature to the value prescribed by the physician, normally between about 32 and 34° C. Cooling of the patient to the target core temperature may be controlled by temperature probes in the patient which are linked to a control unit in the refrigerator/blower unit, so that as the target temperature is approached, the rate of feed of cold air is reduced or its temperature allowed to rise. Some of the air inlet sockets may feed pressurised refrigerated air to the air sacs (71) and the feed to the mattress divided into sections so that different parts of the mattress can be inflated to different pressures to ensure maximum skin contact and support as described, e.g. in U.S. Pat. No. 4,525,885; EPA 034954 and U.S. Pat. No. 5,396,671.

It may also be important to control the rate at which the patient is warmed up again to normal physiological blood temperatures. This may be achieved in accordance with a further aspect of the invention by arranging for the supply of air to the enclosure to be gradually warmed. This can be achieved, for example, by gradually increasing the temperature of the air fed to the connector halves (64), while monitoring the patient's core temperature.

In the embodiments described herein, the enclosure is supported by a combination of factors, including the slight positive pressure of air within the enclosure and the effect of the inflation air within the double-skinned walls and within the inflatable ribs, such as ribs (12) and (61). However, it may be desirable to support the enclosure (or provide extra support) by means of an external frame from which the enclosure is hung by wires, threads, strings or webs. Alternatively, the enclosure may be supported on an internal frame, e.g. comprising a wire frame or poles which may be arranged to locate at their lower ends in recesses in a mattress, bed or other supporting surface. Preferably, the inflatable sacs (71) are also inflated with refrigerated air fed from the refrigerated air supply. Some refrigerated air from the headers (54) is bled off into the space between the double skins of the panels (51) in order to increase the thermal insulation of the enclosure. Air fed into the enclosure from the outlets in the conduits (8) and (12) may leak to atmosphere through stitching or inherent leaks in the enclosure. However, in order to provide a more predictable air flow of refrigerated air from the enclosure, the side or end walls may be provided with outlets 66, preferably near to the foot end of the enclosure.

The material from which the walls and base are made may be moisture vapour permeable. This is perhaps more important for the base so that any sweat or other liquids are evaporated by the flow of air through the sacs of the low air loss mattress, which are also made from moisture vapour permeable material.

What is claimed is:

1. An enclosure for use in cooling a patient to a core temperature below normal body temperature which comprises:
a base portion of sheet material which is joined to an upper portion of sheet material for enclosing a major portion of the patient's body, and
an inflatable rib for holding the upper portion out of contact with the patient's skin,
wherein said base and/or upper portion is associated with a conduit for conducting cooled air to the patient and directing such air to one or more points on the patient's body from which heat loss is rapid.

2. The enclosure of claim 1, wherein the base portion is in the form of a base panel and the upper portion comprises one or more panels which are joined to the base panel by permanent or releasable fastenings to create an enclosure.

3. The enclosure of claim 2 wherein the base panel is connected to at least one header tube extending lengthwise of the panel, said header tube serving to feed cold air to outlets directed onto the patient's body.

4. The enclosure of claim 3 wherein said base panel includes one or more flaps for securing the enclosure to a mattress, bed or other supporting surface.

5. An enclosure for use in cooling a patient to a core temperature below normal body temperature, said enclosure comprising side and end panels and airways for directing cold air on parts of the patient's body from which heat loss is rapid, and header conduits for feeding cold air to the airways, wherein at least one of the panels includes an inflatable rib for assisting in holding the enclosure in an erect position.

6. The enclosure of claim 5 wherein the airways are directed onto the patient' neck and/or groin areas.

7. The enclosure of claim 5 which is secured to an air-inflated mattress and wherein the enclosure includes quick release connectors for connecting the header conduits to a mattress air supply.

8. The enclosure of claim 7 wherein the mattress is a low air loss mattress and the mattress air supply comprises a source of refrigerated air.

9. The enclosure of claim 3 wherein at least the upper panels are double-skinned and means are provided for feeding cold air between the skins of the upper panels to increase the insulation properties of the enclosure.

10. Apparatus for cooling a patient to a core temperature below normal body temperature which comprises:
a first, flexible panel for receiving the patient, one or more other flexible panels which are connected to the first panel and which are foldable over the patient to form an enclosure, wherein said other panels form a wall which is spaced substantially out of contact with the patient's skin at least partially by air pressure within the enclosure which is greater than ambient, and at least one conduit connected to a source of refrigerated air, said base panel being supported on a mattress comprising a plurality of air inflated sacs, said conduit being connected to one or more outlets for directing a stream of air onto the patient's body.

11. The apparatus of claim 10 wherein said conduit extends longitudinally of the base panel.

12. The apparatus of claim 10 wherein said other panels are joined together by a re-sealable closure means to form the enclosure.

13. The apparatus of claim 10 wherein said conduit is connected to the same source of refrigerated air as the inflatable sacs.

14. The apparatus of claim 10 further comprising means for connecting said header to a source of warm air to assist in warming the core temperature of the patient to normal blood temperature.

15. The apparatus of 14 further comprising a means for gradually warming the enclosure while monitoring the patient's temperature.

* * * * *

UNITED STATES PATENT AND TRADEMARK OFFICE
CERTIFICATE OF CORRECTION

PATENT NO. : 6,942,687 B2  Page 1 of 1
APPLICATION NO. : 10/296834
DATED : January 11, 2005
INVENTOR(S) : Hermann Winner et al.

It is certified that error appears in the above-identified patent and that said Letters Patent is hereby corrected as shown below:

On the face of the patent, # (57) Abstract, line 1, change "a passing maneuver, for motor" to --a passing maneuver, motor--

Column 7, line 47, change "which can be reduced" to --which may be reduced--

Column 9, line 24, change "In this specific embodiment," to --In this example embodiment--

Column 10, line 3, change "indicates a desire to pass;" to --indicates a desire to pass; and--

Signed and Sealed this

Twelfth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 6,942,687 B1 Page 1 of 1
APPLICATION NO. : 10/398338
DATED : September 13, 2005
INVENTOR(S) : Keith Patrick Heaton et al.

It is certified that error appears in the above-identified patent and that said Letters Patent is hereby corrected as shown below:

This certificate supersedes Certificate of Correction issued September 12, 2006, the number was erroneously mentioned and should be vacated since no Certificate of Correction was granted for this patent number.

Signed and Sealed this

Twenty-first Day of November, 2006

JON W. DUDAS
*Director of the United States Patent and Trademark Office*